US006146685A

United States Patent [19]

Chrai et al.

[11] Patent Number: 6,146,685

[45] Date of Patent: Nov. 14, 2000

[54] METHOD OF DEPOSITION A DRY POWDER AND DISPENSING DEVICE

[75] Inventors: Suggy S. Chrai, Cranbury; Joseph Thomas McGinn, Flemington; Bawa Singh, Voovhees, all of N.J.

[73] Assignee: Delsys Pharmaceutical Corporation, Monmouth Junction, N.J.

[21] Appl. No.: 09/187,092

[22] Filed: Nov. 5, 1998

[51] Int. Cl.$^{7}$ .......... B05D 1/04

[52] U.S. Cl. .......... 427/2.14; 427/475; 427/486

[58] Field of Search .......... 427/2.14, 180, 427/462, 475, 477, 486; 424/46

[56] References Cited

U.S. PATENT DOCUMENTS 5,470,603 11/1995 Staniforth .
5,714,007 2/1998 Plelcher et al. .

FOREIGN PATENT DOCUMENTS 452 052 10/1948 Canada .
WO93/09832 5/1993 WIPO .

*Primary Examiner*—Fred J. Parker
*Attorney, Agent, or Firm*—Carella, Byrne, et al; Elliot M. Olstein; William Squire

[57] ABSTRACT

A dry powder, for example, a medicament for an inhaler, comprises elongated particles with an aspect ratio sufficient to cause the particles to be bound to a preferably metal or non-metallic sheet material substrate at the particle tips by electrostatic deposition and for aligning a plurality of particles with their major axes aligned normal to the substrate and oriented tip-to-tip. Particles deposited form a low density, high relative void deposition to minimize attractive forces between the particles. This minimizes agglomeration and bonding forces to the substrate facilitating the release of a powdered medicament in an inhaler. Medicament dosages in a substrate pocket are covered by a sealing layer. An embodiment of a drug dosage inhaler substrate and inhaler is disclosed.

10 Claims, 3 Drawing Sheets

METHOD OF DEPOSITION A DRY POWDER AND DISPENSING DEVICE

This invention relates to a method of depositing dry powders on a substrate, and in particular, medicaments for use with inhalers, for example, and inhaler devices for use with such substrates.

CROSS REFERENCE TO RELATED APPLICATIONS AND PATENTS

Of interest are co-pending applications Ser. No. 08/661,213 entitled Inhaler Apparatus with Modified Surfaces for Enhanced Release of Dry Powders filed Jun. 10, 1996 in the name of Datta et al. now U.S. Pat. No. 5,871,010, Inhaler Apparatus with an Electronic Means for Enhanced Release of Dry Powders Ser. No. 08/661,212 filed Jun. 10, 1996 in the name of Sun et al., Ser. No. 08/932,489 entitled Dry Powder Delivery System filed Sep. 18, 1997 in the name of Leedom et al., Ser. No. 08/467,647 entitled Apparatus for Electrostatically Depositing and Retaining Materials Upon a Substrate filed Jun. 6, 1995 now U.S. Pat. No. 5,669,973, Ser. No. 08/506,703 entitled Inhaler Apparatus for Using a Tribo-Electric Charging Technique filed Jul. 25, 1995 now U.S. Pat. No. 5,642,727, Ser. No. 08/659,501 entitled Methods and Apparatus for Electrostatically Depositing a Medicament Powder Upon Predefined Regions of a Substrate filed Jun. 6, 1996 in the name of Pletcher et al., Ser. No. 09/095,246 entitled Dry Powder Deposition Process filed Jun. 10, 1998 in the name of Poliniak et al., all of the foregoing being commonly owned, Ser. No. 09/095,616 entitled Pharmaceutical Product and Method of Making filed Jun. 10, 1998 in the name of Chrai et al., the latter being commonly owned with the assignee of the aforementioned applications and the assignee of the present invention, and U.S. Pat. Nos. 5,714,007, 5,642,727, 5,669,973 commonly owned with the aforementioned applications. All of the aforementioned are incorporated by reference herein in their entirety.

Dry powder inhalers are used as drug delivery devices for pharmaceutical compounds to individuals. In these devices, a pharmaceutical powder is deposited on a surface of a substrate. The substrate may then be supplied in the inhaler as a cassette, a cartridge and so on. When the patient requires medication, the ideal dry powder inhaler forms a fine particle cloud that is to be inhaled and thereby delivers a high respirable fraction of the stored dose deeply into the patients lungs. In most cases, the deep recesses of the lung is the desired site for the drugs in the inhaled powder cloud.

This can be most efficiently achieved by:

1. Releasing a high fraction of the deposited drug and

2. Insuring that the powder cloud consists of individual particles or particle aggregates between 1 μm and 5 μm.

As individual particles are reduced below 10 μm, both release and particle aggregation become serious hindrance to delivering a high respirable fraction deeply into the patient's lungs.

A common problem dealt with by various prior art inhaler apparatuses for dispensing dry powder medicaments is providing for a controlled reliable release of the medicament. The dry powder inhalers may be loaded with medicaments by filling techniques not involving electrostatics. In certain implementations, the deposited powder tends to form agglomerated particles resulting in uncontrolled variation in the amount of medicament released. Several of the aforementioned applications provide various solutions to this problem.

Numerous approaches have been taken in the design of dry powder inhalers. In some cases, the powder is released by impact of a substrate powder carrier, as disclosed in WO 93/09832. Of interest is an inhaler as disclosed in WO 90/13328.

In copending applications Ser. Nos. 661,213 and 661,212, indentations or raised surfaces are disclosed in the inhaler interior surfaces having contact with the medicament for inhalation, the surfaces minimizing the area of contact between the medicament and the surfaces of the inhaler apparatus, promoting the release of the medicament from the inhaler.

Where particles of medicament agglomerate, they impact the mouth and throat rather than remain in the air flow for deposition in the lungs. One remedy is to provide tortuous channels in the inhalers to promote deagglomeration. However, the medicament may be deposited along the channels leading to inaccurate dosage dispensing. Agglomeration also results in the inhaler tending to dispense the medicament inaccurately so that greater or lesser amounts are dispensed. The aforementioned solutions to the problem of agglomeration tend to rely on mechanical devices for minimizing agglomeration effects.

The small particle size required for transport to the lung presents a number of problems for release by the inhaler and delivery to deep lung regions. As the particle size decreases, the relative bonding force between the particle and other objects increases. This applies to both particle-to-substrate bonding and particle-to-particle bonding. As a result, particle aggregates become more tightly bound and individual particles are more difficult to remove from the substrate. Aggregation increases the effective size of the drug released and diminishes the respirable fraction. The increase in relative particle-to-substrate bonding makes drug release more difficult and also decreases the respirable fraction.

The present inventors recognize a need for a different approach wherein the agglomeration itself is minimized so as to be negligible. This reduces the need for mechanical solutions to deal with the agglomeration effects.

A method of depositing a dry powder on a substrate according to the present invention comprises providing a plurality of elongated dry particles each having a longitudinal axis and depositing the particles on a surface of a substrate with the longitudinal axes aligned substantially normal to the substrate surface.

Preferably the method includes in one embodiment charging the particles with a given polarity and electrostatically depositing the particles on the substrate.

In a further embodiment, the particles are provided with an aspect ratio such that an electrical dipole is created in the particles along the axis. An electrical field attracts the particles to the substrate.

In a still further preferred embodiment, the particles have an aspect ratio of about 2:1.

The substrate may be metallic, or non-metallic including mesh and non-mesh materials.

In a further embodiment, a controlled amount of the medicament is deposited at each of a plurality of predetermined regions on the surface of the substrate.

The particles in a further preferred embodiment have a diametrical dimension in the range of about 0.5 μm to 3 μm and a length in the range of about 1 μm to 10 μm.

In a further embodiment, the particles are a pharmaceutically active ingredient medicament.

A device for dispensing a pharmaceutical drug according to a further embodiment of the present invention comprises an inhaler having a mouthpiece and a medicament cavity in communication with the mouthpiece. A dry powder medicament deposited in discrete spaced locations on a substrate is introduced into the cavity for selective dispensing by the inhaler, the medicament comprising a plurality of elongated particles, the particles having an aspect ratio such as to create an electrical dipole in the particles when charged or induced by the depositing field.

A device according to a still further embodiment of the present invention for depositing a dry powder on a substrate comprises a plurality of elongated dry particles each having a longitudinal axis and means for depositing the particles on a surface of a substrate with the longitudinal axes aligned substantially normal to the substrate surface.

IN THE DRAWING

Figure 1:
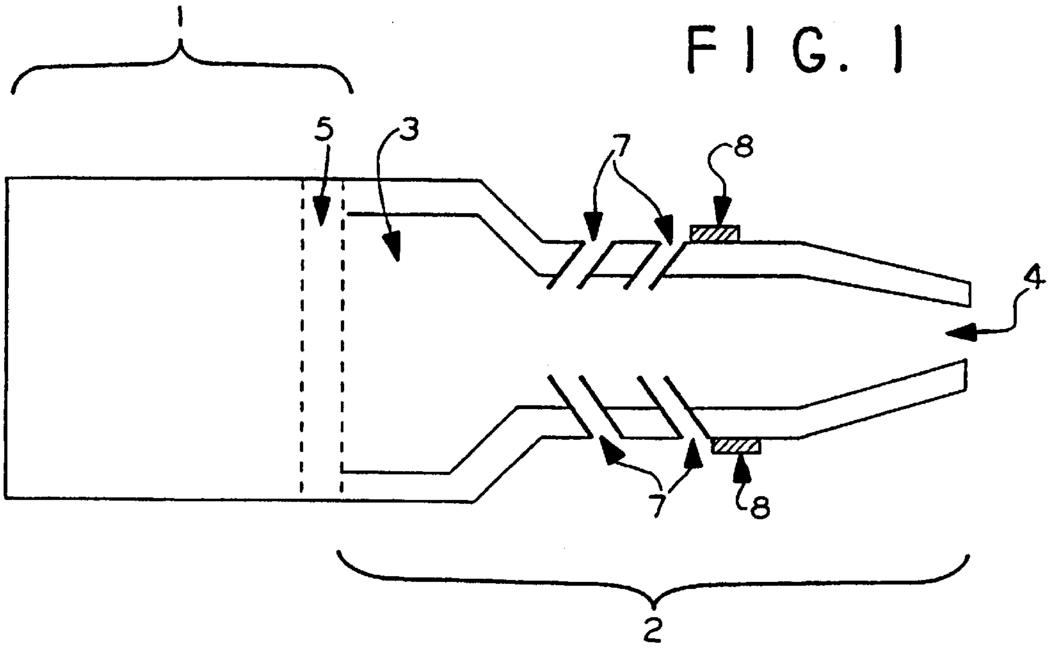
FIG. 1 is a schematic diagram illustrating in general form a deposition process for depositing particles according to an embodiment of the present invention.

In FIG. 1, deposition system 30 is diagrammatically shown and comprises a substrate 32, a charge source 34 for generating a field represented by dashed lines 36, a control 38 and a medicament cloud generator 40 for generating a cloud of elongated medicament particles 42. Generally electrostatic deposition systems are known as described in the aforementioned copending applications and patents. However the disclosed systems may be modified as described herein according to the present invention.

Figure 2A:
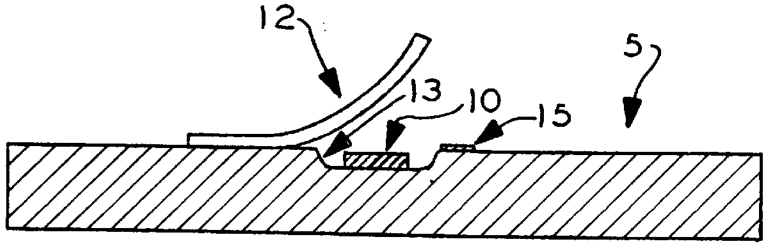
FIG. 2 is a more detailed view of the diagram of FIG. 1 showing field generation on the substrate.
Figure 2B:
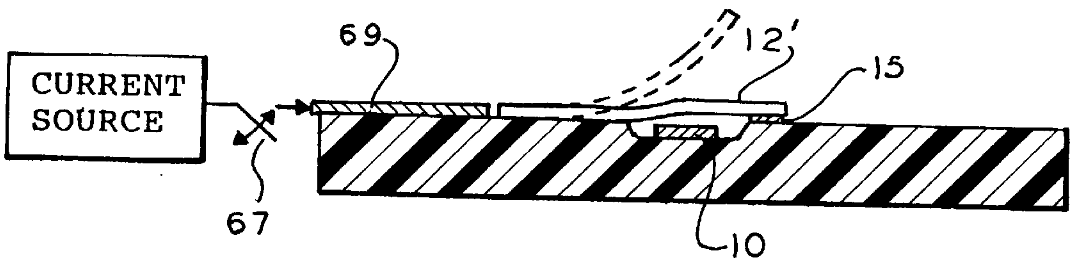

In diagrammatic FIG. 2, in one embodiment, the substrate 32 is at one polarity, e.g., negative charged, and a field electrode 44 is at the opposite polarity, e.g., positive charged. Electrode 44 may surround the substrate 32. Substrate 32 is charged at a local region for receiving the medicament in controlled amounts as described for example in the aforementioned patents and copending applications mentioned in the introductory portion and incorporated by reference herein. Field lines 36 are created between the substrate 32 and the field electrode 44 as shown. Elongated particles 46 in the field exhibiting dipoles align with the field lines 36 and wherein the charges on the substrate 32 attract the particles 46 to the substrate 32.

The medicament powder is in the form of elongated particles having an approximate diameter preferably in the range of about 0.5 to 3 $\mu$m and an axial extent of preferably in the range of about 1 to 10 $\mu$m. The particles are charged with a given polarity in a conventional charging mechanism such as triboelectric chargers, induction charging and so on. The particles are deposited in controlled amounts wherein the amount of active pharmaceutical ingredients deposited at each of a plurality of locations on the substrate does not vary from a predetermined amount, for example, by more than 15%.

Reference is made to the copending applications Ser. No. 09/095,246 entitled Dry Powder Deposition Process filed Jun. 10, 1998 in the name of Poliniak et al. and Ser. No. 09/095,616 entitled Pharmaceutical Product and Method of Making filed Jun. 10, 1998 in the name of Chrai et al. noted in the introductory portion and incorporated by reference herein in their entirety. These applications disclose apparatus and processes for electrostatically depositing pharmaceutically active ingredient medicaments on a substrate including charging a dry powder medicament and electrostatically attracting the charged powder particles to a substrate. In particular, the medicament is deposited in controlled amounts at discrete locations on the substrate wherein the amounts deposited do not vary from a predetermined amount by more than 15%, for example. This process is preferred.

However, other processes for electrostatically depositing dry powder medicaments on a substrate are also disclosed in the aforementioned copending applications and patents noted in the introductory portion, all of which are incorporated by reference herein. Those processes disclose electrostatically depositing controlled amounts of dry powder medicaments on a substrate at discrete locations on the substrate. Variations of the disclosed process herein may be employed to adapt those processes to a metal substrate, whether a tape, mesh or disk with radially extending fingers on which medicaments are deposited as will be described below as employed in the present embodiments. Such variations are within the skill of those of ordinary skill in this art.

In the present invention, elongated dry medicament particles are charged with one polarity, e.g., positive charges and electrostatically deposited on a substrate exposed to an electric field, with a spatial variation arranged to attract the charged particles to discrete predetermined locations on a substrate. This is to be differentiated from prior art processes wherein the particles tend to be generally spherical, amorphous or symmetrical.

Particle removal from surfaces tends to be more difficult as particle size decreases. This is roughly a consequence of the adhesion force decreasing more slowly than the volume and surface area as a particle's size decreases. Since the volume and surface are generally related to removing forces and deaggregation, these forces become increasingly difficult to overcome as the particle size decreases.

Forces of adhesion and agglomeration caused by van der Waal's force increase as the area of contact between a particle and substrate or between two particles increase. If highly elongated particles can be made to deposit on substrates in such a manner that only their tips contact a substrate, adhesion will be lower than if similar particles deposit with their long axes in contact with the substrate. Similarly, agglomeration forces between highly elongated particles will be minimized if they contact tip-to-tip. Agglomeration can also be decreased if the particle density is sufficiently low as to inhibit particle-particle contact along their major axes.

To obtain high respirable fractions, electrostatic deposition is preferred to minimize particle-substrate and particle-particle contact which minimizes adhesive and agglomeration forces respectively. Most if not all pharmaceutical powders are dielectric and can support the separation of electrical charges. In the presence of an electric field, such as the field manifested by lines 36, FIG. 2, particles of such powder tend to become electrically polarized forming dipoles. The particles do not need to be separately charged independently of the field to form such dipoles.

Figure 3:
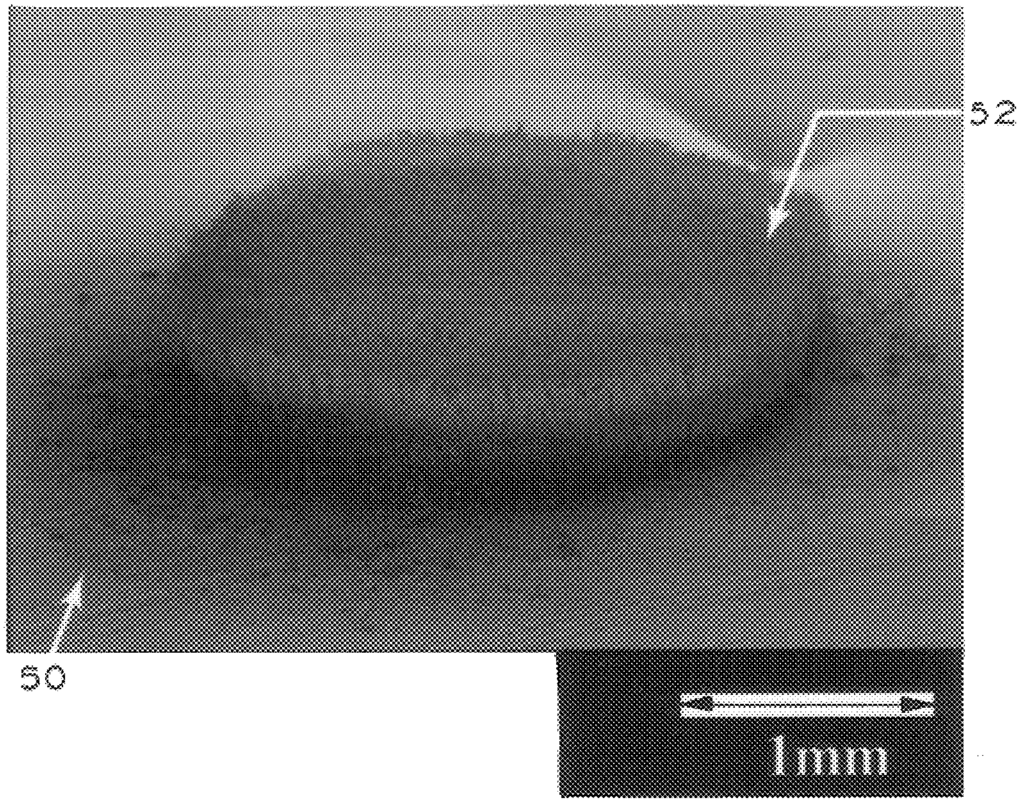
FIGS. 3 and 4 are electronmicrographs illustrating particles deposited on a substrate according to an embodiment of the present invention.
Figure 4:
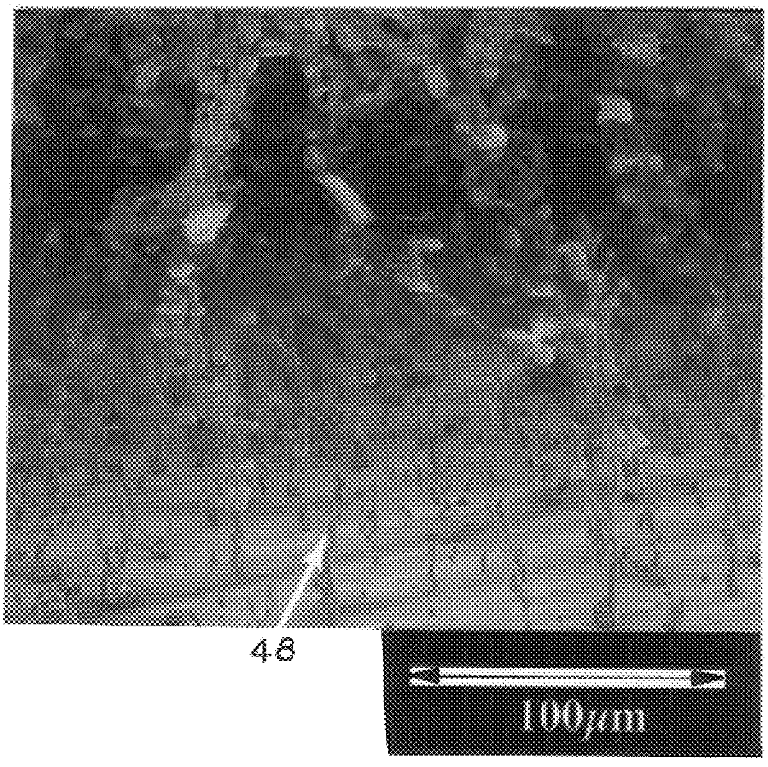

That is, the elongated particles tend to form dipoles with a positive charge at one tip and a negative charge at the opposite tip. A field is applied to the substrate to attract particles charged with a positive polarity, FIG. 2. When the particles are attracted to the substrate by the electric field, the dipole charge in the particles aligns the particles so that their major axis is generally normal to the substrate surface. This attracts the particle tips to the substrate via opposite polarity charges in the substrate field and particle tip. The particles thus stand upright end up on the substrate. FIGS. 3 and 4 are electronmicrographs showing this end-to-end configuration. FIG. 3 shows the grains of a deposited pharmaceutical product at a discrete location on an aluminum substrate. The field aperture 50 outline is shown by scattered particles. The field-defined dose 52 has an open structure as shown in FIG. 3. A comparison of the dose size to grain size is shown by the scale in the figure. FIG. 4 shows the columnar structure of the deposited powder. The scale shows this is an enlargement relative to the scale of FIG. 3.

The higher the aspect ratio of the particles, the greater the polarization. In turn, the polarization of highly acicular particles causes an alignment of the particle's major axis with the electric field line. Introduced charges on insulated dielectric particles will dominate the alignment of the particles.

By controlling the field's geometry, it is possible to align the pharmaceutical particles and direct their deposition to particular locations. For a pre-charged particle, a uniform field will align the particle depending upon its charge distribution. For particles in which polarization is induced by an electrostatic field, alignment will be controlled by the particle geometry, i.e., the long axis is always parallel to the field gradient, FIG. 2. Charged particles will tend to follow field lines. Thus it is advantageous to have a high density of field lines terminating in the preferred deposition site.

FIGS. 3 and 4 show an example of polyethylene glycol (PEG) electrostatically deposited on an aluminum film substrate. The individual particles have an aspect ratio of at least about 2:1 or greater, e.g., 10:1. Once a particle has been deposited, the electrostatic field acts to direct subsequent particles to form elongated chains of tip-to-tip particles. A relative high density of particles on the substrate that may lead to agglomeration of particles along their major axes and may occur under relatively high deposition conditions.

The low-density deposition in which the particle chains remain individually isolated or in single particle thick chains is an ideal structure for release and deaggregation. Individual particles are either bound to the substrate at their tip or to other particles tip-to-tip. In either case, the resultant geometry offers minimum area for van der Waal interaction and subsequently a minimum in adhesive and agglomeration forces.

The density of electrostatic deposited particles is low (i.e., 0.1–0.4 of bulk density) due to the repulsive forces between the particles with the same charge polarity.

For applications requiring doses below approximately 100 $\mu$g, depositions may be made on substrate areas of approximately 50 $mm^2$ without substantial aggregate formation. Consequently, they are isolated or form single-particle-thick chains with low interparticle van der Waal forces and release from the substrate at much lower forces than otherwise would occur.

Figure 5:
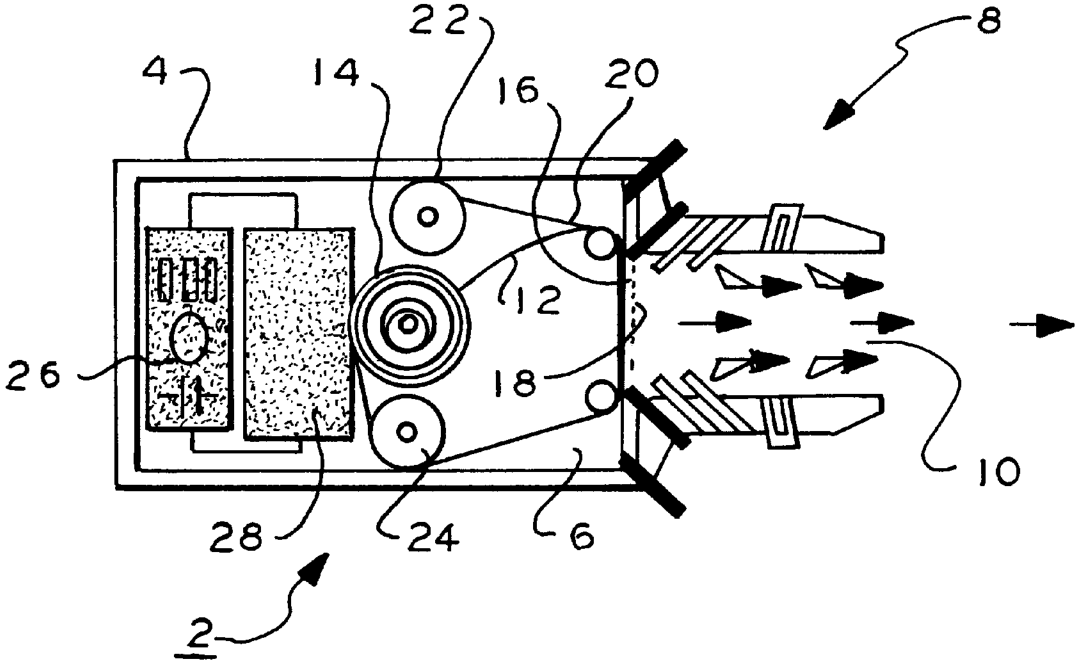
FIG. 5 is a side sectional elevation view of an exemplary inhaler incorporating a medicament deposited according to the present invention.

In FIG. 5, an inhaler apparatus 2, which is given by way of example in one embodiment, comprises a one-piece molded thermoplastic housing 4 having a chamber 6. Other dispensing devices and apparatuses as known in this art may also be employed for dispensing a dry powder active pharmaceutical ingredient medicament. Such other devices may include cassette or cartridge type dispensers.

A mouthpiece 8 may be molded one-piece with and extends from the housing 4 and has a throat 10 in fluid communication with the chamber 6. A medicament dispensing tape 12 is supplied by reel 14. The tape 12 comprises a metal tape substrate 16, preferably stainless steel. Medicament 18 is deposited on the substrate 16 in controlled amounts at each of a plurality of discrete spaced locations. A tape seal 20 covers and protects the medicament 18 on the substrate 16.

The seal 20 is removed by take up reel 22 and the emptied substrate is taken up by take up reel 24. A battery 26 operates an electronic medicament release mechanism 28 (not shown in detail) but described in copending application Ser. No. 661,212 mentioned in the introductory portion and incorporated by reference herein. The inhaler apparatus housing 4, mouthpiece 8, substrate and related mechanisms are described more fully in copending application Ser. No. 661,213 mentioned in the introductory portion and incorporated by reference herein.

Figure 6:
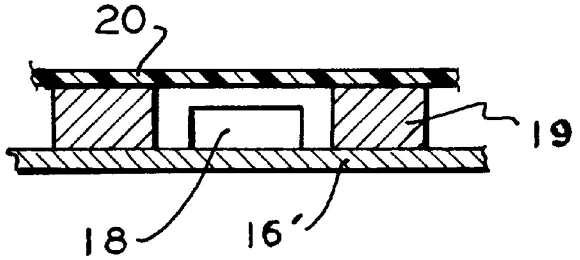
FIGS. 6 and 6*a* are side elevation fragmented sectional views of a representative substrate employed in an inhaler apparatus of an embodiment of the present invention.
Figure 6A:
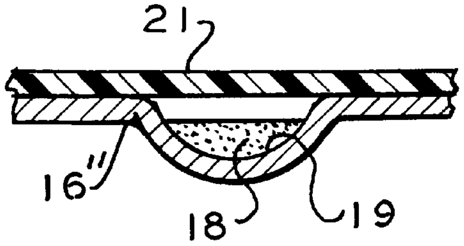

The substrates may be employed in cassettes or cartridges and may be either metal, e.g., stainless steel, or non-metallic as known in this art, may be mesh or solid, and may be of any material suitable as a medicament substrate. The selection of a substrate material depends upon a given implementation. In FIG. 6, substrate 16' may comprise a steel tape having a dosage 18 in discrete locations, a spacer 19 and a sealing tape 20. In the alternative, in FIG. 6*a*, pockets 19, or dimples (not shown) may be formed in the substrate 16". The pockets recesses the dosage 18 and avoids the need for a spacer. This recessing spaces the dosage 18 from the sealing tape 21. When the tape is removed, the dosage remains in place and is not removed by the tape.

It will occur to one of ordinary skill that modifications may be made to the disclosed embodiments without departing from the scope of the invention as defined in the appended claims. For example, the deposited powder may not be a medicament, but may be powders for other applications in accordance with a given implementation. The various substrates are also given by way of illustration. The dispensing device is also by way of example, as other dispensing arrangements may be employed as desired. The description given herein is by way of illustration and not limitation.

What is claimed is:

1. A method of depositing dielectric elongated pharmaceutical active medicament dry powder particles on a substrate comprising:

providing a plurality of said dielectric elongated pharmaceutical active medicament dry particles each having a longitudinal axis; and depositing the particles on a surface of the substrate with the longitudinal axes aligned substantially normal to the substrate surface, the particles being attracted to the substrate by an electric field so as to minimize agglomeration of the particles and to minimize adherence of the particles to the substrate.

2. The method of claim 1 including charging the particles with a given polarity and electrostatically depositing the particles on the substrate.

3. The method of claim 2 including providing the particles with an aspect ratio such that an electrical dipole is created in each particle along its longitudinal axis such that an electrical field electrostatically attracts and aligns the particles to the substrate.

4. The method of claim 1 wherein the particles have an aspect ratio of about 2:1.

5. The method of claim 1 including providing a metal substrate.

6. The method of claim 5 including providing a stainless steel substrate.

7. The method of claim 1 including depositing a controlled amount of the particles at each of a plurality of predetermined regions on the surface of the substrate to form a unit dosage at each said predetermined region.

8. The method of claim 1 including the step of forming particle chains substantially normal to the substrate.

9. The method of claim 1 including providing particles with a diametrical dimension in the range of about 0.5 to 3 $\mu$m and a length in the range of about 1 to 10 $\mu$m.

10. The method of claim 1 including the step of providing a plurality of the particles in a plurality of separate discrete locations on the substrate, each location forming a dosage.

* * * * *